(12) United States Patent
Polkus et al.

(10) Patent No.: US 7,003,145 B2
(45) Date of Patent: Feb. 21, 2006

(54) IMAGE CROPPING FOR ASYMMETRICAL IMAGING

(75) Inventors: Vincent S. Polkus, Delafield, WI (US); Thomas M. Leeds, Pewaukee, WI (US); Mohamed Ali Hamadeh, Waukesha, WI (US); Ping Xue, Cottage Grove, WI (US)

(73) Assignee: GE Medical Systems Global Technology Company, LLC., Waukesha, WI (US)

( * ) Notice: Subject to any disclaimer, the term of this patent is extended or adjusted under 35 U.S.C. 154(b) by 664 days.

(21) Appl. No.: 09/755,238

(22) Filed: Jan. 5, 2001

(65) Prior Publication Data

US 2002/0122534 A1 Sep. 5, 2002

(51) Int. Cl.
*G06K 9/00* (2006.01)

(52) U.S. Cl. .......................... 382/132; 378/19; 378/145

(58) Field of Classification Search ................ 382/128, 382/129, 130, 131, 132, 133, 134, 286, 289; 378/4, 8, 12, 82, 84, 85, 146, 149, 16, 19, 378/113, 145, 10, 11, 22, 39, 46, 55, 63, 90, 378/92, 94, 98.4, 98.8, 101, 116, 147, 167, 378/185, 189; 250/363.04, 363.05, 366, 250/370; 600/472; 356/3.01, 3.1, 307, 603, 356/606, 610, 391, 393
See application file for complete search history.

(56) References Cited

U.S. PATENT DOCUMENTS

| | | | |
|---|---|---|---|
| 4,680,709 A | 7/1987 | Srinivasan et al. ......... 364/414 |
| 4,703,424 A | 10/1987 | Gullberg et al. ............ 364/414 |
| 4,809,312 A * | 2/1989 | Annis ......................... 378/146 |
| 4,891,829 A * | 1/1990 | Deckman et al. .............. 378/4 |
| 5,195,122 A * | 3/1993 | Fabian ....................... 378/165 |
| 5,390,111 A * | 2/1995 | Tam ............................. 378/16 |
| 5,454,019 A | 9/1995 | Migita et al. ................ 378/15 |
| 5,647,018 A | 7/1997 | Benjamin ................... 382/128 |
| 5,742,060 A * | 4/1998 | Ashburn ................ 250/370.09 |
| 5,787,146 A * | 7/1998 | Giebeler ...................... 378/82 |
| 6,226,350 B1 | 5/2001 | Hsieh .......................... 378/98 |
| 6,369,812 B1 * | 4/2002 | Iyriboz et al. .............. 345/419 |
| 6,483,890 B1 | 11/2002 | Malamud ..................... 378/22 |
| 6,516,046 B1 * | 2/2003 | Frohlich et al. ............. 378/65 |
| 6,614,877 B1 | 9/2003 | Anderton ................... 378/98.7 |

* cited by examiner

*Primary Examiner*—Kanjibhai Patel
*Assistant Examiner*—Abolfazl Tabatabai
(74) *Attorney, Agent, or Firm*—Fletcher Yoder (57) ABSTRACT

A technique for selectively processing data from a digital detector includes determining an asymmetrical image area produced by orientation of a radiation source assembly. The assembly may include a radiation source and a collimator, which may be separately orientable. The image area is computed based upon the orientation of the radiation source assembly that projects a radiation beam towards an imaging plane. Image data from a detector within the imaging plane is selectively processed to improve computational efficiency. The system may also determine whether the image area falls within the imaging surface of the detector and inform an operator or inhibit an exposure if such is not the case.

36 Claims, 5 Drawing Sheets

IMAGE CROPPING FOR ASYMMETRICAL IMAGING

FIELD OF THE INVENTION

The present invention relates generally to digital imaging systems, such as digital x-ray imaging systems. More particularly, the invention relates to a technique for cropping or refining image data for more efficient processing when an imaging system is set to create an image off center from a radiation source location.

BACKGROUND OF THE INVENTION

Digital x-ray imaging systems are becoming increasingly widespread for producing digital data which can be reconstructed into useful radiographic images. In current digital x-ray imaging systems, radiation from a source is directed toward a subject, typically a patient in a medical diagnostic application. A portion of the radiation passes through the patient and impacts a detector. The surface of the detector converts the radiation to light photons which are sensed. The detector is divided into a matrix of discrete picture elements or pixels, and encodes output signals based upon the quantity or intensity of the radiation impacting each pixel region. Because the radiation intensity is altered as the radiation passes through the patient, the images reconstructed based upon the output signals provide a projection of the patient's tissues similar to those available through conventional photographic film techniques.

Digital x-ray imaging systems are particularly useful due to their ability to collect digital data which can be reconstructed into the images required by radiologists and diagnosing physicians, and stored digitally or archived until needed. In conventional film-based radiography techniques, actual films were prepared, exposed, developed and stored for use by the radiologist. While the films provide an excellent diagnostic tool, particularly due to their ability to capture significant anatomical detail, they are inherently difficult to transmit between locations, such as from an imaging facility or department to various physician locations. The digital data produced by direct digital x-ray systems, on the other hand, can be processed and enhanced, stored, transmitted via networks, and used to reconstruct images which can be displayed on monitors and other soft copy displays at any desired location. Similar advantages are offered by digitizing systems which convert conventional radiographic images from film to digital data.

In certain type of imaging systems, such as digital x-ray systems, the radiation source may be positioned at various locations along an imaging area, with the detector typically being positioned at a corresponding location. For example, the source and detector may be moved along a longitudinal centerline of a patient support and, in certain systems, in a direction transverse to the centerline. Such positioning is useful for imaging specific anatomies or limbs, while exposing a patient to a minimal level of radiation.

In digital imaging systems, the computational load imposed on the image data processing circuitry is related to the amount of information collected. For larger or higher resolution images, or images employing a greater dynamic range for each pixel, significant quantities of data may be collected and processed to obtain the final data set used to reconstruct the image. Where smaller areas are imaged, such as specific anatomies in x-ray systems, electronic cropping may be used to reduce the total amount of data collected or processed. In general, such cropping entails selectively sampling or processing data from those pixels corresponding to the desired image area, the remaining pixels being considered to contain little or no usefull information.

For asymmetrical imaging (i.e. where the source is angularly positioned with respect to a projection line through the source and orthogonal to the detector and/or where the image center is not coincident with the detector center), no effective automated digital cropping technique has been developed. Consequently, in such cases, an operator or clinician may be required manually to view the image and crop the data after processing.

There is a need, therefore, for an improved image data cropping technique which will allow for automated digital cropping of image data in asymmetrical imaging situations. There is a particular need for an approach which permits the quantity of data sampled or processed to be reduced and which reduces the need for clinicians to manually view and crop resulting images.

SUMMARY OF THE INVENTION

The present invention provides a technique for cropping image data designed to respond to these needs. The technique may be used in newly-installed systems, but may be easily retrofitted into existing systems to enhance performance and reduce computational loads. While the technique may be used in a wide range of system types, it is particularly well-suited to digital x-ray systems which permit asymmetrical imaging by translating and/or tilting (rotating) a radiation source assembly, or by swiveling the associated beam collimation device with respect to an imaging plane.

The technique allows for determining the projection area of an imaging beam, such as an x-ray beam, on the basis of system geometry. In particular, the technique may take into account various spatial and angular positions and rotational positions of both a radiation source and a collimator, which, in combination, may result in various forms and orientations of an imaging projection on the image plane. In a full implementation, angular translation and rotation can be implemented for both the source and the collimator in three independent directions in space. More limited implementations may be envisioned, in which angular position and rotation are more limited, such as angular position of a source with respect to a centerline of the system only. The technique also allows for determining whether the projection area falls within a detector framework or boundaries. Thus, in addition to limiting the amount of data sampled, and improving the computational efficiency of the system, the technique may be used to avoid unnecessary exposure to radiation, or to limit radiation exposure to a usefull area of a detector.

The algorithm also includes the condition where the x-ray beam is not angulated but rather offset with respect to a condition where the beam and detector centers are coincident. This specific case is possible when the x-ray field size is less than that of the detector and the central ray is orthogonal to the detector plane. In this situation, the operator is able to displace the source assembly with respect to the detector center and still produce an acceptable diagnostic image that fully captures the anatomical features of the region of interest. (This is possible by comparing the predicted coordinates of the x-ray beam impingement points/vertices with the coordinates of the detector edge and cropping the image if those coordinates are contained in the space occupied by the image detector. The algorithm also accommodates beam angulation in the generalized formulation. When there is no beam angulation, diagonal terms of the transformation matrices become 1 (cosine (0)).

DETAILED DESCRIPTION OF THE INVENTION

Figure 1:
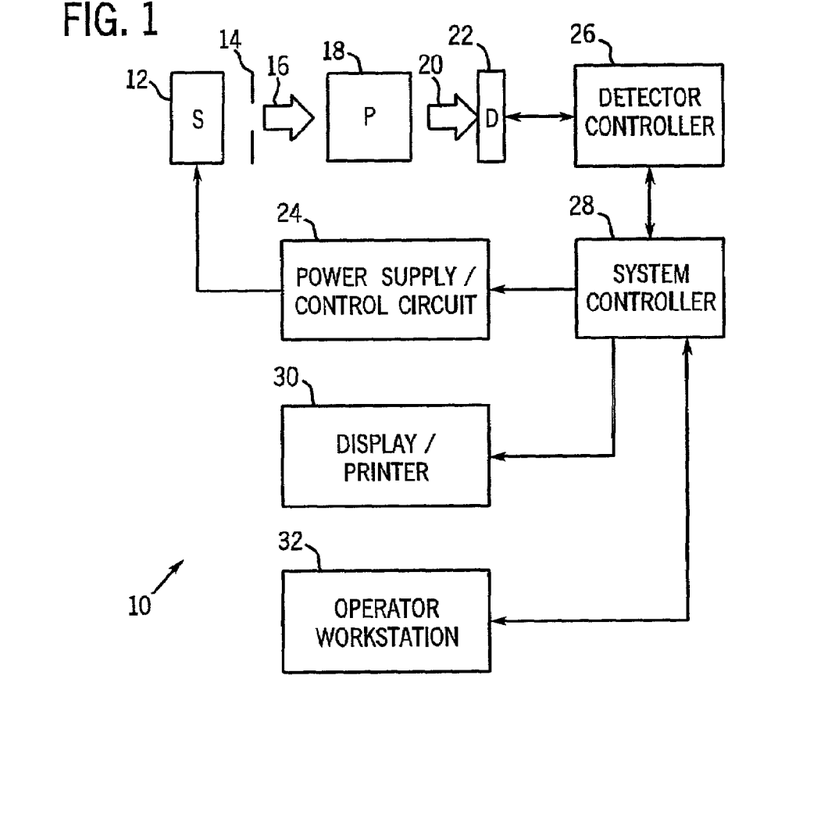
FIG. 1 is a diagrammatical overview of a digital x-ray imaging system in which the present technique is incorporated.

FIG. 1 illustrates diagrammatically an imaging system 10 for acquiring and processing discrete pixel image data. In the illustrated embodiment, system 10 is a digital x-ray system designed both to acquire original image data, and to process the image data for display in accordance with the present technique. In the embodiment illustrated in FIG. 1, imaging system 10 includes a source of x-ray radiation 12 positioned adjacent to a collimator 14. Collimator 14 permits a stream of radiation 16 to pass into a region in which a subject, such as a human patient 18 is positioned. A portion of the radiation 20 passes through or around the subject and impacts a digital x-ray detector, represented generally at reference numeral 22. As described more fully below, detector 22 converts the x-ray photons received on its surface to lower energy photons, and subsequently to electric signals which are acquired and processed to reconstruct an image of the features within the subject.

Source 12 is controlled by a power supply/control circuit 24 which furnishes both power and control signals for examination sequences. Moreover, detector 22 is coupled to a detector controller 26 which commands acquisition of the signals generated in the detector. Detector controller 26 may also execute various signal processing and filtration functions, such as for initial adjustment of dynamic ranges, interleaving of digital image data, and so forth. Both power supply/control circuit 24 and detector controller 26 are responsive to signals from a system controller 28. In general, system controller 28 commands operation of the imaging system to execute examination protocols and to process acquired image data. In the present context, system controller 28 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 28 is linked to at least one output device, such as a display or printer as indicated at reference numeral 30. The output device may include standard or special purpose computer monitors and associated processing circuitry. One or more operator workstations 32 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
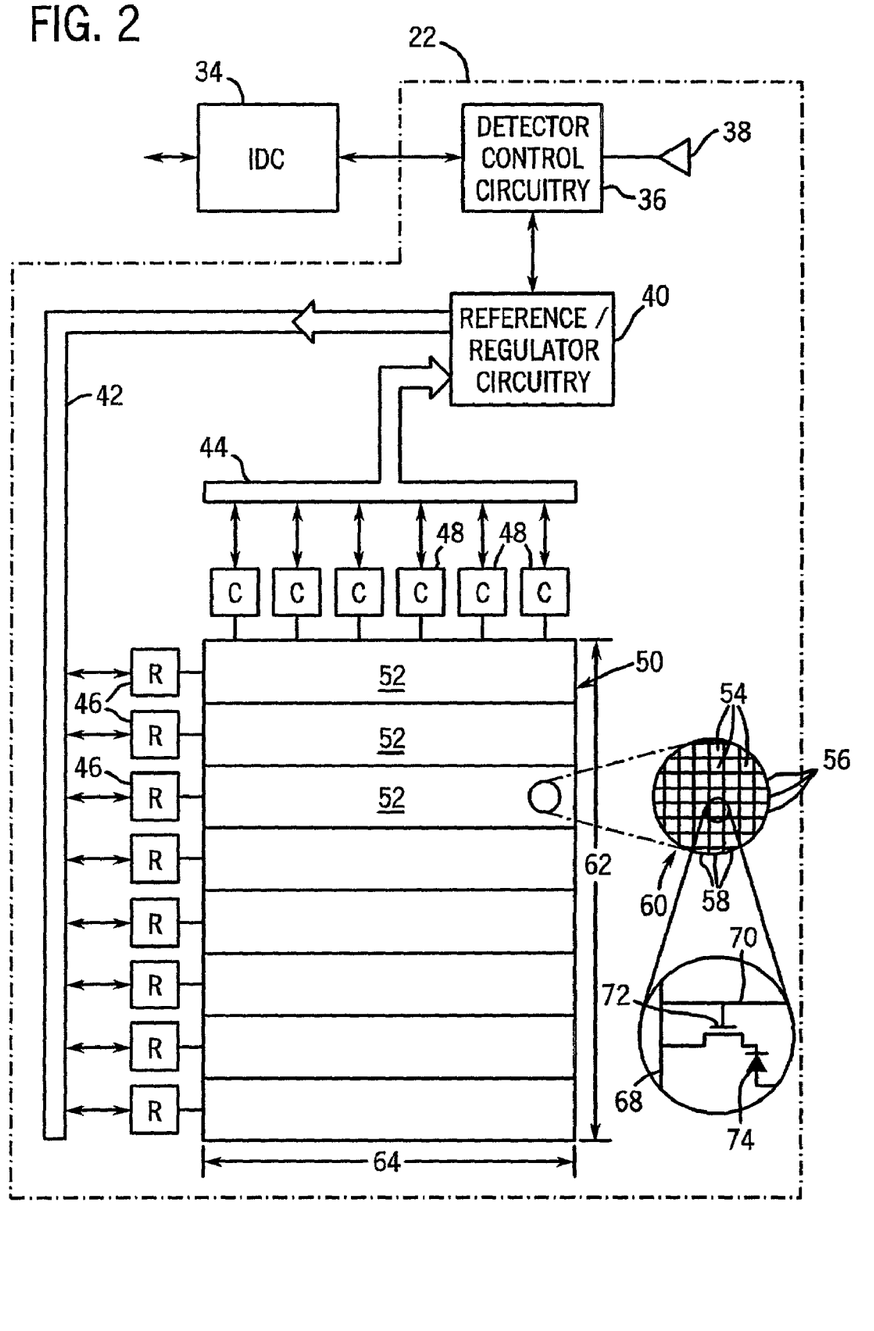
FIG. 2 is a diagrammatical representation of certain of the functional circuitry for producing image data in a detector of the system of FIG. 1 to produce image data for reconstruction.

FIG. 2 is a diagrammatical representation of functional components of digital detector 22. FIG. 2 also represents an imaging detector controller or IDC 34 which will typically be configured within detector controller 26. IDC 34 includes a CPU or digital signal processor, as well as memory circuits for commanding acquisition of sensed signals from the detector. IDC 34 is coupled via two-way fiberoptic conductors to detector control circuitry 36 within detector 22. IDC 34 thereby exchanges command signals for image data within the detector during operation.

Detector control circuitry 36 receives DC power from a power source, represented generally at reference numeral 38. Detector control circuitry 36 is configured to originate timing and control commands for row and column drivers used to transmit signals during data acquisition phases of operation of the system. Circuitry 36 therefore transmits power and control signals to reference/regulator circuitry 40, and receives digital image pixel data from circuitry 40.

In a presently preferred embodiment illustrated, detector 22 consists of a scintillator that converts x-ray photons received on the detector surface during examinations to lower energy (light) photons. An array of photodetectors then converts the light photons to electrical signals which are representative of the number of photons or the intensity of radiation impacting individual pixel regions of the detector surface. Readout electronics convert the resulting analog signals to digital values that can be processed, stored, and displayed, such as in a display 30 or a workstation 32 following reconstruction of the image. In a present form, the array of photodetectors is formed on a single base of amorphous silicon. The array elements are organized in rows and columns, with each element consisting of a photodiode and a thin film transistor. The cathode of each diode is connected to the source of the transistor, and the anodes of all diodes are connected to a negative bias voltage. The gates of the transistors in each row are connected together and the row electrodes are connected to the scanning electronics. The drains of the transistors in a column are connected together and an electrode of each column is connected to readout electronics.

In the particular embodiment illustrated in FIG. 2, by way of example, a row bus 42 includes a plurality of conductors for enabling readout from various columns of the detector, as well as for disabling rows and applying a charge compensation voltage to selected rows, where desired. A column bus 44 includes additional conductors for commanding readout from the columns while the rows are sequentially enabled. Row bus 42 is coupled to a series of row drivers 46, each of which commands enabling of a series of rows in the detector. Similarly, readout electronics 48 are coupled to column bus 44 for commanding readout of all columns of the detector.

In the illustrated embodiment, row drivers 46 and readout electronics 48 are coupled to a detector panel 50 which may be subdivided into a plurality of sections 52. Each section 52 is coupled to one of the row drivers 46, and includes a number of rows. Similarly, each column driver 48 is coupled to a series of columns. The photodiode and thin film transistor arrangement mentioned above thereby define a series of pixels or discrete picture elements 54 which are arranged in rows 56 and columns 58. The rows and columns define an image matrix 60, having a height 62 and a width 64.

As also illustrated in FIG. 2, each pixel 54 is generally defined at a row and column crossing, at which a column electrode 68 crosses a row electrode 70. As mentioned above, a thin film transistor 72 is provided at each crossing location for each pixel, as is a photodiode 74. As each row is enabled by row drivers 46, signals from each photodiode may be accessed via readout electronics 48, and converted to digital signals for subsequent processing and image reconstruction.

Figure 3:
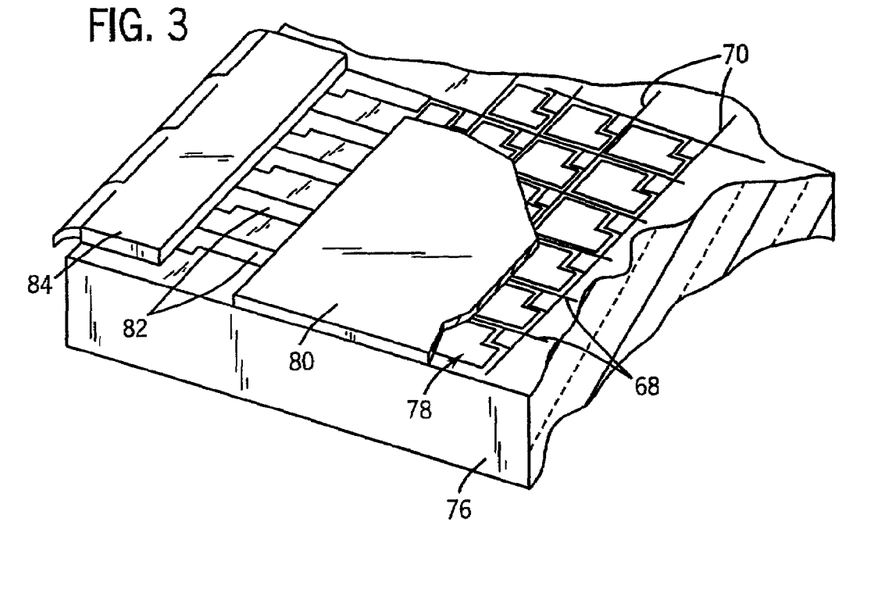
FIG. 3 is a partial sectional view illustrating an exemplary detector structure for producing the image data.

FIG. 3 generally represents an exemplary physical arrangement of the components illustrated diagrammatically in FIG. 2. As shown in FIG. 3, the detector may include a glass substrate 76 on which the components described below are disposed. Column electrodes 68 and row electrodes 70 are provided on the substrate, and an amorphous silicon flat panel array 78 is defined, including the thin film transistors and photodiodes described above. A scintillator 80 is provided over the amorphous silicon array for receiving radiation during examination sequences as described above. Contact fingers 82 are formed for communicating signals to and from the column and row electrodes, and contact leads 84 are provided for communicating the signals between the contact fingers and external circuitry.

Figure 4:
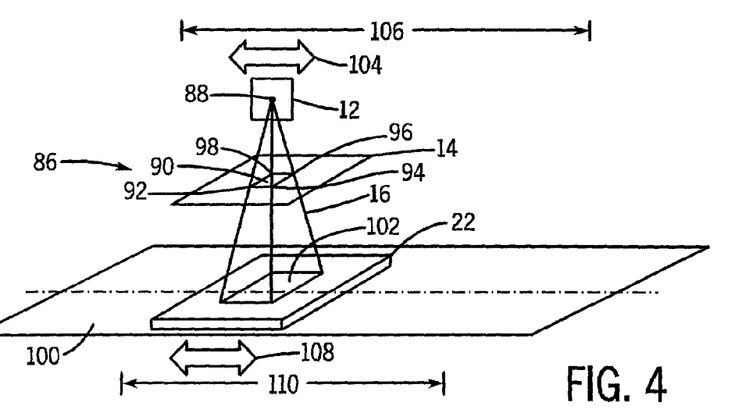
FIG. 4 is a diagrammatical perspective view of an x-ray imaging system of the type shown in FIG. 1, and illustrating ranges of movement of a source and detector along an imaging area.

The foregoing exemplary imaging system may permit various types of alternative positioning of the x-ray source, the beam collimator, and the detector to allow for considerable latitude in selecting a segment of a subject which will be imaged. FIG. 4 illustrates ranges of movement of a source and a detector along an imaging area. As shown in FIG. 4, the source 12 projects a beam 16 of radiation through collimator 14 toward the detector 22. In the system arrangement of FIG. 4, designated generally by the reference numeral 86, an effective point source 88 of radiation is contained within the source 12 and is projected through an aperture 90 in the collimator. In the illustrated example, aperture 90 is square or rectangular, lending to the beam a similar shape, as defined by straight lines joining points or vertices 92, 94, 96 and 98. As will be appreciated by those skilled in the art, in practice, the beam may radiate well beyond the bounds of aperture 90, with the aperture serving to direct a portion of the beam to the detector within the desired imaging area.

An imaging or impingement plane 100 generally corresponds to a surface on which or adjacent to which a patient is positioned in a medical diagnostic imaging application. In other contexts, the plane may serve as support or background for other types of objects. An impingement or imaging area 102 is defined where the beam 16, shaped by the collimator aperture 90, impinges the plane 100. To permit selection of the region along plane 100 to be imaged, the source 12 may be moved as indicated by reference numeral 104, along a range of movement 106. In the illustration of FIG. 4, the range 106 is generally along or parallel to a longitudinal centerline of the plane 100. Similar movement 108 is available for the detector 22, along a range of movement 110. In general, collimator 14 is displaced with the radiation source, the two forming a radiation source assembly, although rotational and angular positioning of the collimator may be provided independent of the rotational or angular position of the source and described below.

Figure 5:
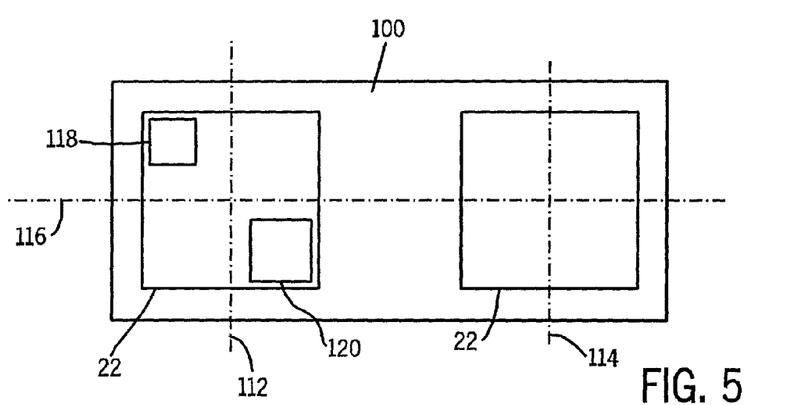
FIG. 5 is a plan view of image areas of the type obtainable through proper adjustment of the arrangement of FIG. 4.

Exemplary projections of beam 16 in plane 100 of the arrangement of FIG. 4 are illustrated in FIG. 5. As shown in FIG. 5, limits 112 and 114 on the movement of the detector 22 will typically impose corresponding limits on the range of imaging areas available. However, where the source and/or collimator may be moved along a further range and angularly positioned with respect to a centerline 116 of the system, various projection areas may be obtained. For example, asymmetrical imaging applications may permit projections 118 and 120 to be formed off of centerline 116. While in the simplified illustration of FIG. 5, these areas have generally rectangular shapes, in practice, their shapes may be manipulated by appropriate angular positioning and rotation of the source and/or collimator as described more fully below.

As will be appreciated by those skilled in the art, projections off of centerline 116 may be extremely useful in reducing radiation exposure, while allowing for imaging of selected anatomies or features of a patient or subject. Where a detector 22 provides an area substantially larger than the image area, however, sampling of the entire detector, and processing of image data from the entire detector matrix can result in substantial computational loads. To provide greater computational efficiency, therefore, the present technique provides for selective processing or "digital cropping" of the image data in such applications.

Figure 6:
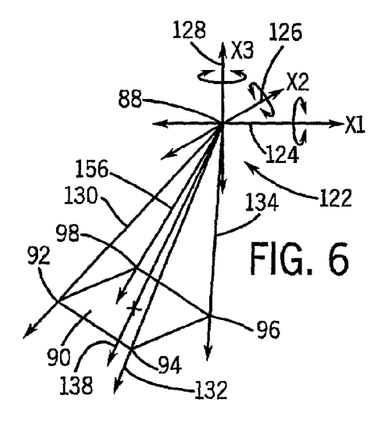
FIG. 6 is a diagrammatical illustration of a coordinate system for movement of a radiation source in the arrangement of FIG. 4.
Figure 7:
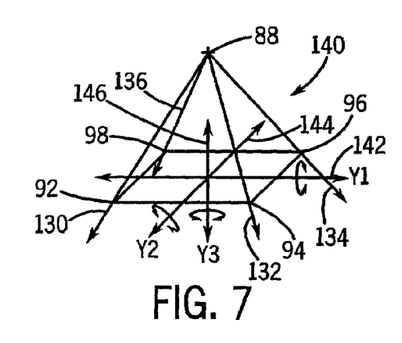
FIG. 7 is a diagrammatical illustration of a coordinate system for movement of a collimator in the arrangement of FIG. 4.

In the analysis of the image for determining a projection area for cropping, reference may be made to coordinate systems for angular positioning and rotation of both the radiation source and the collimator. FIGS. 6 and 7 illustrate various degrees of freedom of motion of a source and a collimator, respectively, in a system of the type illustrated in FIG. 4. In particular, FIG. 6 represents a coordinate system 122 in which the radiation source may be translated angularly, and rotated. As noted above, the beam from the point source 88 is formed or shaped by the opening in the collimator, such as corresponding to vertices 92, 94, 96 and 98 and the edges extending therebetween. Where the system permits, however, the source may be positioned with respect to mutually orthogonal coordinate axes, such as an X1 axis 124, an X2 axis 126, and an X3 axis 128. In addition to angular positioning within this coordinate system 122, the source may be provided with freedom of rotational movement about the axis or any combination of the axes. Resulting projection lines extending through the corners of the collimator aperture are thereby defined as indicated by lines 130, 132, 134 and 136 in FIG. 6. Moreover, a centerline passing through the midpoint of the collimator is defined as indicated at reference numeral 138. Again, it should be noted that the lines illustrated in FIG. 6 are simply projections of the beam limits following collimation, and do not necessarily correspond to the shape of the beam prior to impingement with the collimator.

In certain systems and where desired, similar freedom of movement may be provided for the collimator to allow further shaping of the image area. As illustrated in FIG. 7, with respect to the point source 88, the collimator coordinate system 140 may provide for translation along and rotation about additional mutual orthogonal axes, including a Y1 axis 142, a Y2 axis 144 and a Y3 axis 146. Again, the lines of projection of the beam from the point source 88 will be defined by the shape of the aperture in the collimator limited by vertices 92, 94, 96 and 98 and the joining edges, as indicated by lines 130, 132, 134 and 136 in FIG. 7.

Figure 8:
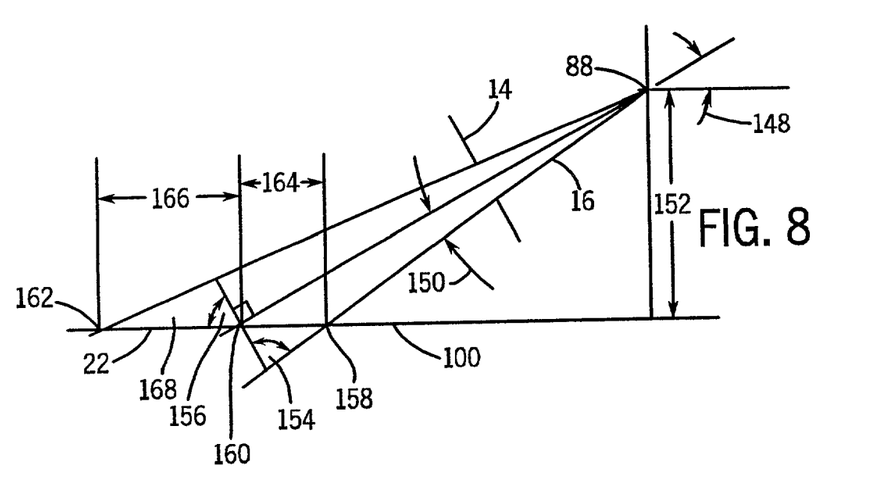
FIG. 8 is an elevational view of an x-ray beam from a source directed to a detector in an exemplary asymmetrical imaging application.
Figure 9:
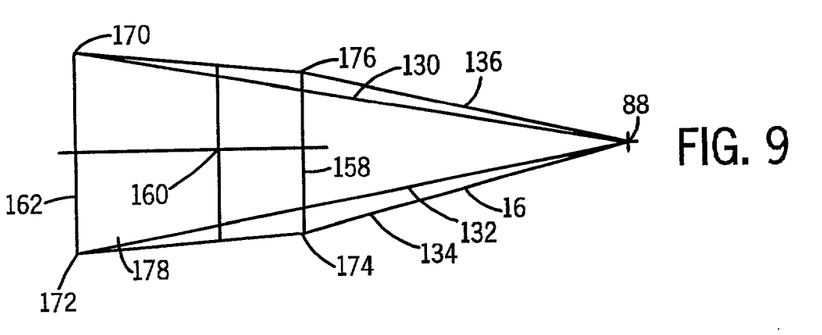
FIG. 9 is a plan view of the same beam.

By adjustment of the source and collimator positions, various projections may be obtained for the image area. An exemplary positioning for these elements is illustrated in FIGS. 8 and 9. In the elevational view of FIG. 8, a point source 88 has been rotated off of an orthogonal line between the source and an imaging plane 100. The resulting beam 16, as limited by collimator 14, is projected toward a detector 22. In the example illustrated in FIG. 8, the beam 16 has been rotated about an angle 148 with respect to a horizontal line parallel to the image plane. An angle 150 is therefore defined between the inner limit of the beam and the beam center. The point source is located a known distance 152 from the image plane, commonly referred to as the source-to-image distance, or SID. (When the X-Ray beam is angulated, the vertical SID 152 is equal to the actual SID times the cosine of the included angle. When there is no beam angulation, vertical and actual SID are identical.)

Given the geometry set forth in FIG. 8, several angles and distances may be computed. For example, an internal angle 154 is defined between the projected boundary of beam 16 and a plane orthogonal to the beam centerline. Another angle 156 is defined between the image plane 100 and the same plane orthogonal to the beam centerline. Because the distance of the collimator from the point source 88 and the opening in the collimator will generally be known, as will the SID 152, angles 154 and 156 permit computation of the locations at which the beam impinges the image plane 100, as indicated by point 158, point 160, and point 162 in FIG. 8. It should be realized that, while appearing as a point in the projection of FIG. 8, in practice, the impingement locations will typically correspond to lines delimiting the impingement or imaging area. The corresponding distances between these points, as designated by reference numeral 164 and 166 can thereby be computed as well. Finally, as also illustrated in FIG. 8, the computation of the relevant geometries permits a region 168 wherein the beam impinges the detector surface to be identified for verification purposes as described more fully below.

A plan view of the projection of FIG. 8 is illustrated in FIG. 9. As shown in FIG. 9, the beam 16 propagates, as shaped by the collimator, along a region defined by lines 130, 132, 134 and 136, to impact the area on the image plane as set forth above. Where a trapezoidal area such as that illustrated in FIG. 9 is produced by the beam, it will be noted that the center of the beam impinges the image plane at a location 160 which is not centered with respect to the other boundaries 158 and 162. In general, however, the projection will be determined by the shape and configuration of the beam, and the orientation of the source and detector with respect to the image plane, so as to produce a corresponding image area bounded by vertices 170, 172, 174 and 176 at locations where the corresponding lines 130, 132, 134 and 136 project to the image plane. The image area 178, then, corresponds to the area where the useful image data should be collected, and thereby to the area which can be cropped for enhanced image processing.

With the foregoing geometry and coordinate systems in mind, analysis of the relevant data to determine an area to be digitally cropped proceeds generally as follows. In a present implementation algorithm, position feedback and known geometric information on the relationships between the components, particularly the source, the detector, and the image plane, are referenced. The spatial points of the vertices of the collimator field are first computed using coordinate transformation matrices that are established with angular position feedback of the system. That is, because the angular positions of the source and collimator will be known (e.g., sensed), as will their rotational orientations if such freedom of movement is provided, the locations in space of the vertices of the collimator aperture, denoted by reference numerals 92, 94, 96 and 98 in the foregoing discussion, will be computed. Successive rotations or angular displacement of the radiation source about the focal spot or the point source 88 can be managed through appropriate manipulation of the associated transformation matrices to compute the spatial coordinates of the vertices in the global (i.e., unrotated) coordinate system.

The present implementation of the transformation matrices will now be discussed with reference to a straightforward application in which the radiation source is rotated about axis 126 (See FIG. 6) by an angle $\phi$ and the collimator is swiveled about the axis 146 (See FIG.) by an angle $\Phi$.

For collimator swivel, the following rigid body transformation matrix is applicable:

$$[\varphi] = \begin{bmatrix} \cos(\varphi) & -\sin(\varphi) & 0 \\ \sin(\varphi) & \cos(\varphi) & 0 \\ 0 & 0 & 1 \end{bmatrix},$$

where $\Phi$ is the angle of rotation of the beam-formatting collimator about a vertical axis Y3 (axis 146 in FIG. 7) through that device (which can be thought of as the central x-ray beam). Similarly, for rigid body rotations of the collimator about the fixed X2 axis (axis 126 in FIG. 6), the following transformation matrix is applicable:

$$[\phi] = \begin{bmatrix} \cos(\phi) & 0 & \sin(\phi) \\ 0 & 1 & 0 \\ -\sin(\phi) & 0 & \cos(\phi) \end{bmatrix}.$$

With respect to the coordinate system of the collimator with the origin of the focal point (i.e., the point source 88), each vertex has coordinates that remain constant but that change with respect to the fixed coordinate system. The matrices for these vertices are represented by vector components in the coordinate system 140 illustrated in FIG. 7:

$$[P]_i = \begin{bmatrix} P_{1,i} \\ P_{2,i} \\ P_{3,i} \end{bmatrix},$$

where i=1, 2, 3, 4 are the coordinates of the corners 92, 94, 96 and 98 of the collimator aperture, respectively. Similarly, a vector exists for the central ray of the system within the collimator. The actual components of [P] depend upon the basic geometry of the collimator as well as the field size set for the diagnostic examination.

The ensuing computational process involves determining the coordinates of the rotated vectors in the initial unrotated coordinate system. This calculation can be represented by the equation:

$$[P] = [\phi][\Phi][P]_i$$

The computed components represent direction values that are unique for each directed line segment (lines 130, 132, 134 and 136 in the foregoing discussion). These direction values are then used to establish the parametric form of the lines in three-dimensional space to determine the intersection of the lines with the image plane of the detector. The computational algorithm, in a present implementation, uses the following series of equations:

$$\frac{X_1 - X_1^0}{P_{1,i}} = \frac{X_2 - X_2^0}{P_{2,i}} = \frac{X_3 - X_3^0}{P_{3,i}}.$$

By selecting the origin of coordinates to coincide with the focal point (i.e., the point source 88 discussed above), the values $X_1^0$, $X_2^0$, and $X_3^0$ become zero.

It should be noted that this restriction can be removed to assess the affects of non-coincidence between the focal spot and the rotational center of the diagnostic source assembly. Utilizing the source-to-image feedback distance from the system (distance 152 in the projection of FIG. 8), the variable $X_3$ becomes a known value in the series of parametric equations (equal to the SID), and the intersection coordinates $X_1$ and $X_2$ can be computed. Similarly, the predicted intersection point of the center ray of the beam with the detector or image plane can be computer with the associated direction values.

As will appreciated by those skilled in the art, the foregoing approach permits the location of the intersection points of the x-ray beam with the image plane to be computed based upon the known geometry of the system. These points, corresponding to points 170, 172, 174 and 176 in the example illustrated in FIG. 9, provide the parameter vertices for the image to be cropped. Where desired, then, the detector or the detector control circuitry discussed above can command sampling of rows and columns only corresponding to the area bounded by these vertices and their joining lines. Alternatively, additional information can be sampled, but only information relating to this portion of the detector surface need be processed.

As noted above, the present technique also permits comparison of the actual position of the detector with respect to the image area provided by the beam. This may be desired, for example, to establish whether the predicted vertices of the x-ray beam actually impinge the detector. Because the detector and the diagnostic radiation source assemblies are independent, it is possible for them to be spatially misaligned. In the present implementation correlation between the detector position and the beam impingement area is accomplished by comparing the predicted positions of the beam impingement area to the detector imaging surface location to establish whether the image area within the physical confines of the detector.

To implement this feature of the technique, boundaries of the detector are established with respect to the calibrated center of the detector in accordance with the relationships:

$$X_d - W/2 X_{imp} X_d + W/2,$$

and $$Y_d - W/2 Y_{imp} Y_d + W/2,$$

where $X_d$ and $Y_d$ represent the extremities of the image area, W represents the detector width, and $X_{imp}$ and $Y_{imp}$ represent the coordinates in the image plane where the center of the beam impinges the image plane.

With the preceding information the algorithm is capable of computing whether the impingement or image area corresponds to the limits of the detector (i.e., is encompassed by the detector imaging surface). Where such is not the case, an operator may be notified via an alert to correct the detector position or the size and orientation of the projected image area, or the exposure may be inhibited.

Figure 10:
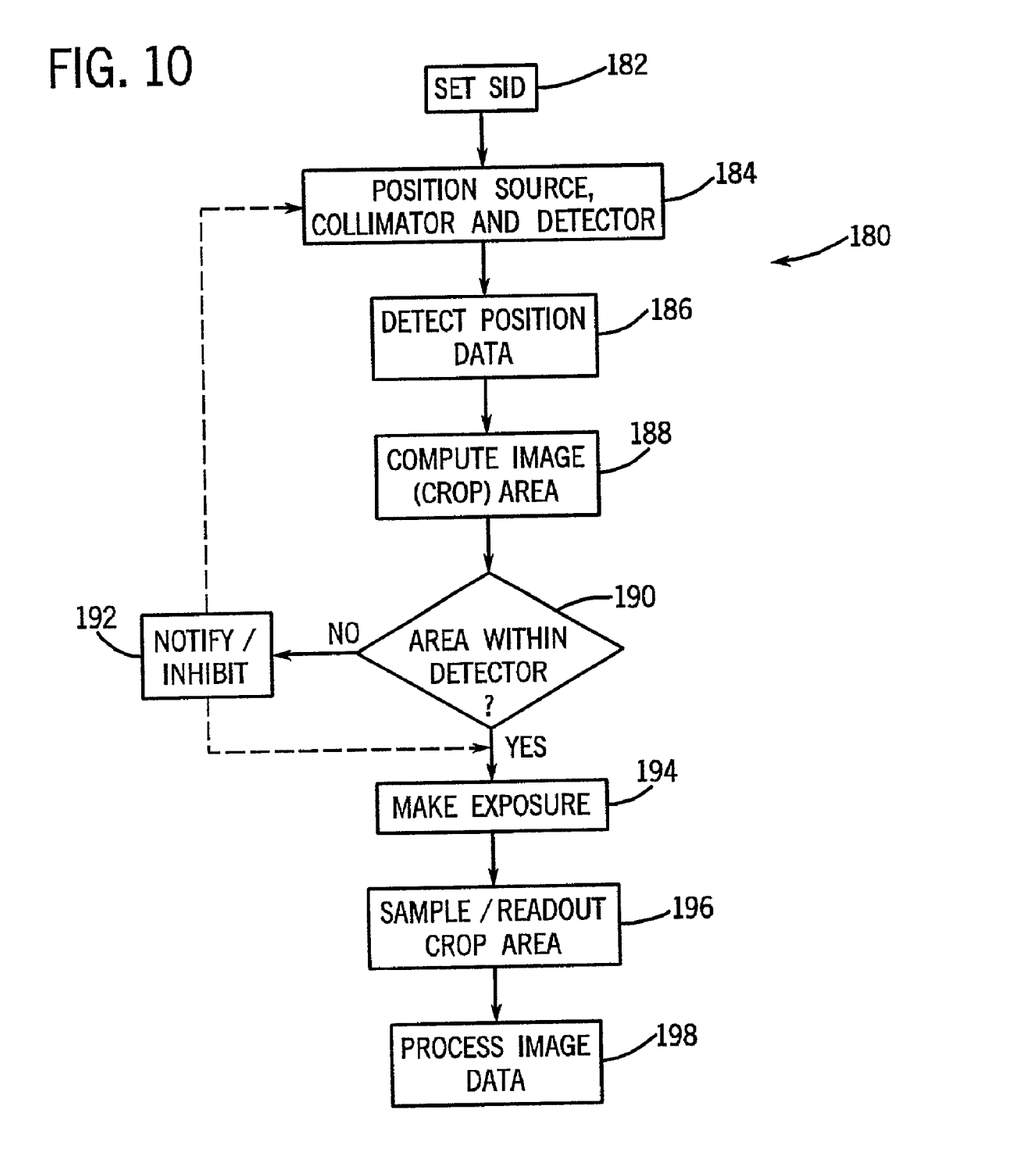
FIG. 10 is a flow chart illustrating exemplary logic in performing digital cropping of an image taken in an asymmetrical imaging application.

The foregoing process is set forth diagrammatically in the flow chart of FIG. 10. In the logic of FIG. 10, denoted generally by the reference numeral 180, the SID is first set as indicated at reference numeral 182. At step 184, the source, collimator and detector are positioned, with the source and collimator being angularly positioned and rotated in accordance with the degrees of freedom available in the particular imaging system. At step 186 the position data regarding the angular displacement of the source and collimator, and their rotation, if any, is detected. Such detection may be carried out in any of a range of manners, such as via conventional position sensors. At step 188 the image area is computed as discussed above with reference to the transformation matrices and the SID. With the impingement points in the image plane thus identified, the process may determine whether the image area is within the detector imaging surface bounds as indicated at step 190. As such is not the case, as discussed above, the operator may be notified, or the imaging sequence may be inhibited as indicated at step 192. Once appropriate correction has been made, or if the impingement area is found to be within the bounds of the detector, the desired exposures may be made as indicated at step 194. The image data are then read out and cropped, either during the readout process or subsequently thereto, as indicated at step 196. Finally, the image data may be processed in a conventional manner as indicated at step 198.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method for cropping an asymmetrical digital image, the method comprising the step of:
   identifying a projection of a radiation beam in an image plane, the projection being asymmetrical with respect to an axis of the image plane; and
   processing image data for a portion of a digital detector based upon the identified projection.

2. The method of claim 1, wherein the step of identifying the projection includes sensing orientation of a radiation source and computing locations of incidence of the radiation beam in the image plane.

3. The method of claim 1, wherein the step of identifying the projection includes sensing orientation of a collimator and computing locations of incidence of the radiation beam in the image plane.

4. The method of claim 1, wherein the projection is identified based upon spatial location of a collimator aperture and on a transfonnation matrix for a radiation source.

5. The method of claim 1, wherein the projection is identified based upon spatial location of a collimator aperture and on a transformation matrix for the collimator.

6. The method of claim 1, wherein processing the image data includes sampling image data from the detector only from an area encompassing the projection.

7. The method of claim 1, wherein processing the image data includes storing only image data from an area encompassing the projection.

8. The method of claim 1, comprising the further step of determining whether the projection is encompassed within bounds of the detector.

9. The method of claim 8, comprising the further step of generating an operator alert if the projection is not encompassed within bounds of the detector.

10. The method of claim 1, wherein the radiation beam may be angularly oriented and rotationally shaped with respect to the image plane, and wherein the projection is identified based upon angular orientation and rotational shaping with respect to an orthogonal orientation.

11. A method for cropping data in a digital x-ray imaging system, the method comprising the steps of:
orienting a radiation beam to project the beam towards an image plane to impinge the plane asymmetrically with respect to an axis of the plane and to impinge a region of a detector extending in the image plane, the region being smaller than an imaging surface of the detector;
computing an image area over which the beam impinges the plane; and
processing image data from the region of the detector including the image area.

12. The method of claim 11, wherein the radiation beam is oriented by angular positioning of a radiation source.

13. The method of claim 11, wherein the radiation beam is oriented by rotational positioning of a radiation source.

14. The method of claim 11, wherein the radiation beam is oriented by angular positioning of a collimator.

15. The method of claim 11, wherein the radiation beam is oriented by rotational positioning of a collimator.

16. The method of claim 11, wherein the image area is computed by determining projections of portions of the beam based upon orientation of the beam.

17. The method of claim 11, comprising the step of determining whether the image area is encompassed by the imaging surface of the detector.

18. The method of claim 17, comprising the step of generating an operator alert if the image area is not encompassed by the imaging surface of the detector.

19. The method of claim 11, wherein only image data for the region is sampled form the detector.

20. The method of claim 11, wherein the region includes portion of an image matrix of rows and columns of pixels, the portion of the image matrix fully encompassing the image area.

21. A method for processing image data in a digital x-ray imaging system, the method comprising the steps of:
orienting a radiation beam producing assembly to project an x-ray beam towards an image plane to impinge the plane asymmetrically with respect to an axis of the plane and to impinge a region of a detector extending in the image plane, the region being smaller than an imaging surface of the detector;
sensing orientation of the radiation beam producing assembly;
computing an image area over which the beam impinges the plane;
generating the x-ray beam; and
processing image data from the region of the detector including the image area.

22. The method of claim 21, wherein the radiation beam producing assembly includes a radiation source and a collimator.

23. The method of claim 22, wherein the radiation source and the collimator are configured to allow freedom of orientation with respect to one another.

24. The method of claim 23, wherein the orientations of the radiation source and the collimator are separately sensed in accordance with respective coordinate systems.

25. The method of claim 24, wherein the image area is computed based upon transformation matrices for the coordinate systems.

26. The method of claim 21, wherein the image area is computed based upon projection of the beam through an aperture in a collimator.

27. The method of claim 21, comprising the further step of determining whether the image area is encompassed by the imaging surface of the detector.

28. The method of claim 27, comprising the step of generating an operator alert if the image area is not encompassed by the imaging surface of the detector.

29. The method of claim 27, comprising the step of inhibiting generation of the x-ray beam if the image area is not encompassed by the imaging surface of the detector.

30. A digital x-ray system comprising:
a radiation source assembly orientable with respect to an imaging plane to produce an asymmetrical image area;
a digital detector extending in the imaging plane and having an imaging surface larger than the image area; and
a control circuit configured to compute the image area based upon orientation of the radiation source assembly and to process image data from the detector for the image area to the exclusion of data from portions of the imaging surface outside the image area.

31. The system of claim 30, wherein the radiation source assembly includes an x-ray source and a collimator.

32. The system of claim 31, wherein the radiation source and the collimator are orientable with respect to one another.

33. The system of claim 31, wherein the control circuit is configured to compute the image area based upon projection of an x-ray beam through an aperture in a collimator.

34. The system of claim 31, wherein the control circuit is further configured to determine whether the image area is encompassed by the imaging surface.

35. The system of claim 34, wherein the control circuit is further configured to generate an operator alert if the image area is not encompassed by the imaging surface.

36. The system of claim 34, wherein the control circuit is further configured to inhibit initiation of an x-ray exposure if the image area is not encompasses by the imaging surface.

* * * * *